(12) United States Patent
Mäusezahl et al.

(10) Patent No.: US 12,426,778 B2
(45) Date of Patent: Sep. 30, 2025

(54) METHOD FOR ASCERTAINING PHYSIOLOGICALLY CORRECT BIOMETRIC DATA OF AN EYE

(71) Applicant: Carl Zeiss Meditec AG, Jena (DE)

(72) Inventors: Holger Mäusezahl, Jena (DE); Roland Bergner, Jena (DE); Manfred Dick, Gefell (DE)

(73) Assignee: Carl Zeiss Meditec AG, Jena (DE)

(*) Notice: Subject to any disclaimer, the term of this patent is extended or adjusted under 35 U.S.C. 154(b) by 743 days.

(21) Appl. No.: 17/762,537

(22) PCT Filed: Aug. 3, 2020

(86) PCT No.: PCT/EP2020/071765
§ 371 (c)(1),
(2) Date: Mar. 22, 2022

(87) PCT Pub. No.: WO2021/058183
PCT Pub. Date: Apr. 1, 2021

(65) Prior Publication Data
US 2022/0378288 A1 Dec. 1, 2022

(30) Foreign Application Priority Data
Sep. 26, 2019 (DE) .................. 10 2019 214 784.4

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/0041* (2013.01); *A61B 3/1005* (2013.01);
(Continued)

(58) Field of Classification Search
CPC ... A61B 3/0025; A61B 3/0041; A61B 3/1005; A61B 3/101; A61B 3/102; A61B 3/103;
(Continued)

(56) References Cited

U.S. PATENT DOCUMENTS

2007/0171365 A1 7/2007 Tuan
2010/0002192 A1 1/2010 Hara
(Continued)

FOREIGN PATENT DOCUMENTS

EP 2 786 698 A1 10/2014
JP H03-257 039 A 11/1991
(Continued)

OTHER PUBLICATIONS

International Preliminary Report on Patentability for PCT/EP2020/071765, issued Mar. 15, 2022, 8 pages.
(Continued)

*Primary Examiner* — Wyatt A Stoffa
*Assistant Examiner* — Rahman Abdur
(74) *Attorney, Agent, or Firm* — DeWitt LLP (57) ABSTRACT

A method for collecting biometric measurement data of an eye on the basis of different measurement modalities, allowing for physiologically correct, representative, and robust biometric measurement data. In the method, the measurement data for individual measurement variables and the dynamic behavior of the eye are recorded continuously at the highest possible repetition rate over the measurement time. The individual phases of the dynamics of the eye which define the limits of the phase for stable vision are analyzed on the basis of the measurement values, and only the measurement data for the individual measurement variables are output which have been detected during the phase for stable vision. Although the proposed method is provided for collecting biometric measurement data in preparation for
(Continued)

a cataract operation, the method can also be applied to other areas of ophthalmology to generate error-free measurement data or recordings of the eye.

21 Claims, 4 Drawing Sheets

(51) Int. Cl.
*A61B 3/103* (2006.01)
*A61B 3/107* (2006.01)
*A61B 3/11* (2006.01)
*A61B 3/117* (2006.01)
*A61B 3/14* (2006.01)

(52) U.S. Cl.
CPC .............. *A61B 3/101* (2013.01); *A61B 3/102* (2013.01); *A61B 3/103* (2013.01); *A61B 3/107* (2013.01); *A61B 3/112* (2013.01); *A61B 3/1173* (2013.01); *A61B 3/14* (2013.01)

(58) Field of Classification Search
CPC ....... A61B 3/107; A61B 3/112; A61B 3/1173; A61B 3/14
USPC ......................................................... 351/206
See application file for complete search history.

(56) References Cited

U.S. PATENT DOCUMENTS

| | | |
|---|---|---|
| 2013/0162946 A1 | 6/2013 | Dobashi |
| 2015/0150450 A1 | 6/2015 | Nozato |
| 2015/0272434 A1 | 10/2015 | Satake |
| 2016/0135681 A1* | 5/2016 | Wakil ................. A61B 3/107 606/4 |
| 2017/0192502 A1 | 7/2017 | Dmitrieva |
| 2017/0325681 A1 | 11/2017 | Orlowski |
| 2019/0038126 A1 | 2/2019 | Copland |

FOREIGN PATENT DOCUMENTS

| | | |
|---|---|---|
| WO | WO 2010/117386 A1 | 10/2010 |
| WO | WO 2019/141750 A1 | 7/2019 |

OTHER PUBLICATIONS

International Search Report for PCT/EP2020/071765, mailed Nov. 19, 2020, 4 pages.
English translation of International Search Report for PCT/EP2020/071765, mailed Nov. 19, 2020, 2 pages.
Search Report for DE 20 2019 214 784.4 dated Jun. 16, 2020, 8 pages.
Brochure; "Der neue IOLMaster 700"; Carl Zeiss Meditec Ag; DE 32_010_000911; Germany CZ-I/2015.
Hoffmann, Peter; "Diagnostik vor Kataraktoperationen bei Implantation torischer Linsen"; Teil 3: Fehlerquellen—erreichbare Genauigkeit; Ophthalmo-Chirurgie 25: 265-270 (2013).
Werkmeister, R. M. et.al; "Measurement of Tear Film thickness using Ultrahigh Resolution OCT"; Clinical Trials; IOVS 2013; 5578-5583.

* cited by examiner

METHOD FOR ASCERTAINING PHYSIOLOGICALLY CORRECT BIOMETRIC DATA OF AN EYE

RELATED APPLICATIONS

This application is a National Phase entry of PCT Application No. PCT/EP2020/071765 filed Aug. 3, 2020, which application claims the benefit of priority to DE Application No. 10 2019 214 784.4, filed Sep. 26, 2019 the entire disclosures of which are incorporated herein by reference.

TECHNICAL FIELD

The invention relates to a method for collecting biometric measurement data of an eye on the basis of various measurement modalities, said method facilitating physiologically correct, representative and robust biometric measurement data.

BACKGROUND

The preparation of a cataract operation on the human eye requires various biometric measurement data of the patient's eye in order to be able to calculate the suitable refractive power for the artificial intraocular lens (IOL) to be implanted.

Different measuring devices are used to this end in the known prior art. Many such measuring devices are based on optical methods, for example:
- A keratometer/ophthalmometer for measuring the surface curvature of the cornea,
- A topography device for measuring the entire cornea,
- An autorefractometer for establishing the objective refraction (visual acuity test),
- A pupillometer for determining the width and light reactivity of the pupil,
- A pachymeter for measuring the corneal thickness,
- etc.

Measuring devices for determining distances in the eye, based either on ultrasound or likewise using optical methods, are known. These include Scheimpflug cameras, slit lamps and measuring devices based on methods from optical coherence tomography (OCT), partial coherence interferometry (PCI) or the like.

To carry out highly precise, contactless measurements, solutions based on the OCT methods have prevailed in the prior art. In this case, measurements are implemented in the form of depth scans and not, like in the case of the Scheimpflug cameras and slit lamps, in the form of sectional images.

Combination measuring devices that merge two or more measuring systems in one device have also become established in the prior art.

In this respect, reference for example is made to the IOLMaster® 700 by Zeiss. This combination device determines the surface curvature of the cornea using a keratometer, and axis length, anterior chamber depth and lens thickness by application of OCT. Additionally, further parameters of the eye, such as what is known as the white-to-white distance, are determined. On the basis of these measurement values, which form the basic parameters for calculating an IOL, it is possible to carry out a calculation by application of various calculation formulae, or else a ray tracing calculation.

A high accuracy in the determination of biometric measurement data on the eye has already been reached to date. Nevertheless, various sources of error can still have a negative influence on the measurement results and thus lead to a non-optimal calculation of the IOL to be implanted.

The further optimization of the calculation of IOLs to be implanted was considered in [2] listed below, in particular for the implementation of the toric IOLs.

However, no further improvements could be found to date. The prior art merely proposes the introduction of a plurality of measurements with subsequent averaging of the measurement values in order to obtain a more reliable result by way of a mean measurement value.

Currently, the procedure when determining biometric measurement data of the eye of a patient according to the prior art is as follows, within the scope of which the patient is asked:
- where possible not to blink following an eyelid movement,
- to open the eye as far as possible and
- to fixate on a static target (usually a light dot or image).

This should ensure that a stable tear film is present, the eyelid is open far enough and the eye is fixated without accommodating.

Once the patient's eyes have been adjusted to the measuring device in this way, a measurement is carried out at any desired time. Typically, the measurement data are acquired within a second, so as not to burden the patient too much and so as to reliably catch their attention.

Consequently, the measurement data acquisition is arbitrary and depends on the operator or on automatically processed indicators such as, for example, the centration of the eye on the measuring axis, the attainment of a sharp image representation of the eye in a camera or the like.

A disadvantage of this procedure is that the optical-physiological state of the corneal surface or of the eye is unknown at the actual time of measurement data acquisition.

There can be strongly deviating measurement values or even incorrect measurements at disadvantageous measurement times, which may then lead to a deterioration in the visual function following the implantation of an IOL.

It should be noted that the dynamics of the living patient's eye have previously not been given sufficient consideration during biometric measurements.

In principle, the dynamics of the living patient's eye have not been examined in any more detail during these measurements either until now, as a result of which the measurement errors emerging as a result have not been able to be avoided.

LITERATURE

[1] Brochure; "Der neue IOLMaster 700"; Carl Zeiss Meditec AG; DE_32_010_000911; Germany CZ-I/2015
[2] Hoffmann, Peter; "Diagnostik vor Kataraktoperationen bei Implantation torischer Linsen"; Teil 3: Fehlerquellen—erreichbare Genauigkeit; OPHTHALMO-CHIRURGIE 25: 265-270 (2013)
[3] Werkmeister, R. M. et. al; "Measurement of Tear Film thickness using Ultrahigh Resolution OCT"; Clinical Trials; IOVS 2013; 5578-5583

SUMMARY OF THE INVENTION

Embodiments of the invention include a method for collecting biometric measurement data of an eye which are physiologically correct, representative and robust. In the process, the measurement data acquisition may additionally be dependent on the optical-physiological state of the eye and should be recorded and evaluated as automatically as possible.

Embodiments of the invention include a method for determining physiologically correct biometric measurement data of an eye by selecting dynamic measurement data by virtue of the measurement data of the individual measurement quantities being recorded continuously over the measurement time at the highest possible repetition rate and, additionally, the dynamic behavior of the eye being recorded continuously over the measurement time at the highest possible repetition rate. The individual phases of the dynamics of the eye are analyzed from these measurement values, the limits for the phase of stable vision are defined and only the measurement data of the individual measurement quantities which were acquired during the phase of stable vision are output.

According to the invention, the dynamic behavior of the eye is recorded in the process on the basis of one, more or else all of the following criteria:
tear film,
opening of the eyelid,
fixation,
accommodation and
adaptation.

Although the proposed method is provided in particular for collecting biometric measurement data of an eye in preparation for a cataract operation, it may also be applied in different fields of ophthalmology in order to generate error-free measurement data or recordings of the eye.

BRIEF DESCRIPTION OF THE DRAWINGS

The invention is described in more detail below on the basis of example embodiments. In this respect.

DETAILED DESCRIPTION

On account of the explained prior art and the highlighted problems, example embodiments of the invention register the dynamic properties of the eye during biometric measurements or else refractive or other diagnostic measurements and only selects and provides the physiologically correct, usable biometric parameters for further processing.

In the example method for determining physiologically correct biometric measurement data of an eye by selecting dynamic measurement data, the measurement data of the individual measurement quantities are recorded continuously over the measurement time of approximately 20 s (a plurality of eyelid movements) at the highest possible repetition rate.

According to example embodiments of the invention, the dynamic behavior of the eye is additionally recorded continuously over the measurement time at the highest possible repetition rate, the individual phases of the dynamics of the eye are analyzed and the limits for the phase of stable vision are defined.

As a result of the method, only the measurement data of the individual measurement quantities assigned to the phase of stable vision are output or considered for the subsequent calculations.

In particular, these biometric measurement data of the patient's eye are required to be able to calculate the refractive power of a suitable artificial intraocular lens (IOL) to be implanted.

The calculation of an IOL is implemented by application of one of the various existing calculation formulae or by application of a ray tracing calculation. By way of example, the following measurement data can be recorded using the method described:
radii and axes of the anterior corneal surface,
radii and axes of the posterior corneal surface,
pachymetry of the cornea,
anterior chamber depth,
radii and thickness of the lens,
tilt of the lens
eye length,
white-to-white distance,
distance from the retinal pigment epithelium to the inner limiting membrane,
pupil diameter and
refraction.

This list is purely an example and makes no claim of completeness.

In this context, it should be mentioned that the measurement time for the continuous recording of the measurement data of the individual measurement quantities is at least 1 s, for example 20 s.

According to example embodiments of the invention, provision is made for collecting measurement values at different measurement times, but in each case within the range of stable vision C within a typical measurement window of the measuring device of approximately 0.5-1.5 s and the formation of a mean value from approximately 10-15 individual measurements. This measurement value determined according to the invention from the mean values of the measurement window within the range of stable vision, like for example the radius of the cornea directly from this measurement, is representative for the range of stable vision of the patient. As an alternative to the mean value of the measurement values at different measurement times in the range of stable vision C, the use of the median value or any other aggregated value from these measurement values is envisaged according to the invention. A decision regarding use in this context is made on the basis of the respectively obtained quality of the clinical results. For the first time, these filtered measurement results allow the collection of physiologically correct and robust measurement data for the examined eye and the discrimination of disturbing dynamic effects of said eye.

There should for example be a plurality of eyelid movement cycles within an overall measurement time duration.

Longer measurement times can be introduced should there be a need for more measurement data. An overall measurement time of approximately 1 min should usually not be exceeded in the case of a biometric examination.

This is the only way to ensure that the concentration of the patient or examiner is not excessively strained, the attentiveness of the patient is ensured and also the optical radiation exposure of the patient is kept minimal. Furthermore, the amount of data collected should not exceed an advantageous amount within the meaning of processability and value for the measurement accuracy.

According to example embodiments of the invention, the dynamic behavior of the eye is recorded on the basis of one, some of or else all of the following criteria:

tear film (indirectly by the change in the keratometer values),
opening of the eyelid,
fixation,
accommodation and
adaptation.

Fundamentally what is provided is that at least one stable measurement phase is determined by at least one measuring modality.

In this case, it is particularly advantageous, for example, if a stable measurement phase is determined by one measuring modality and correlated in time with at least one second measuring modality which is likewise influenced by the dynamic profile of the first measurement data. Thus, reliable measurement data of the second and also further measurement modalities can likewise be transmitted with high reliability to the output of the measuring device, with averaging of the measurement data additionally being able to be implemented. Furthermore, the median value or any other aggregated value of the measurement data can be used.

According to an advantageous example configuration, the analysis of the individual phases of the dynamics of the eye is implemented on the basis of various criteria, with the limits for the phase of stable vision arising from the overlap thereof.

According to a further advantageous example configuration, the analysis of the individual phases of the dynamics of the eye is implemented on the basis of various criteria, for which different limits for the phase of stable vision are defined. In this case, only the measurement data of the individual measurement quantities recorded during the various phases of stable vision are used, for example for forming a mean value and/or median value, and output.

In accordance with a first example embodiment, the tear film of the eye is recorded for the dynamic behavior of said eye, by virtue of the radius of curvature of the cornea or of the precorneal tear film being measured and analyzed between two eyelid movements. In this case, it should be noted that the topography or keratometry of the precorneal tear film is assessed as topography or keratometry of the cornea.

Great dynamics on the eye are present by virtue of the formation of the tear film and its dissolution. Thus, according to [2], the blinking frequency of an adult is approximately 12 eyelid movements/min and the eyelids distribute the precorneal tear film (uniformly according to the prior art) over the surface of the eye within 0.3-1 s. On average, the tear film has a layer thickness of approximately 5 μm [3], which is no longer present following a tear film breakup and consequently represents a variable quantity. To measure the radii and topography of the corneal front side, which has approximately ⅔ of the refractive power of the eye, optical reflection methods based on point patterns (keratometer/ophthalmometer) or on the basis of so-called Placido rings (topography device) are ultimately used to evaluate their reflection image on this variable precorneal tear film in order to determine the measurement values.

Figure 1:
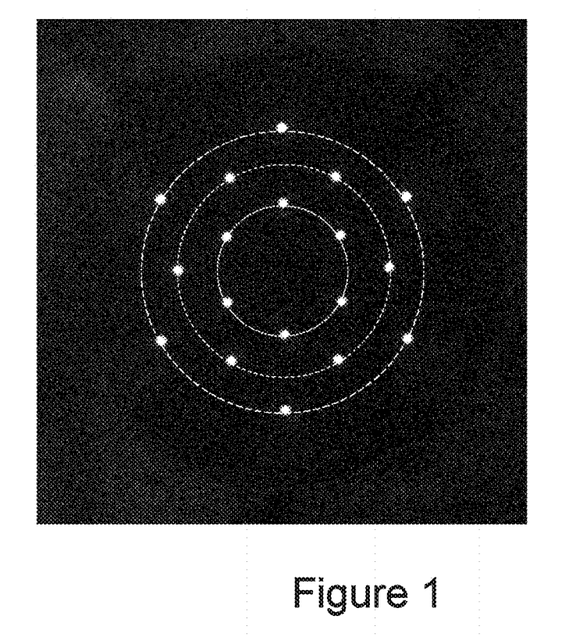
FIG. 1 depicts a static reflection image of a keratometer.

In this respect, FIG. 1 depicts a static reflection image of a keratometer, the 18 measurement points of which are arranged in three rings with different diameters, the central ring offset from the others.

On account of the large refractive index difference between air and precorneal tear film, the pachymetry of the cornea and the eye length should also always capture this one measurement point (corneal front surface with tear film), which is subject to the dynamics of the tear film.

Therefore, patients are requested to blink and then keep the eye open in the prior art, in order to be able to carry out the measurement with a "good" tear film.

To date, all current, aforementioned measuring devices have not been able to take account of the dynamic effects of the tear film and therefore obtain measurement results which are influenced by these dynamics and which may not be representative for the physiologically correct value of the measurement quantities. This state represents a substantial source of error within the scope of biometric measurements on the eye.

Triggers for the eyelid movement are receptors on the corneal surface, which signal a thin tear film (tear film breakup). As a result, the optical system and hence also the visual sense of vision worsen. During the eyelid movement, the visual perception is completely suppressed in the relevant regions of the brain. Just after the eyelid movement, the visual perception still is briefly restricted until a stable clean tear film has formed on the entire corneal surface. At this instant, the active visual perception and processing of the visual stimuli by the brain start. A time interval of a plurality of seconds, during which human vision it works optimally, starts. This interval is a quasi-stationary state in which the measurement values are very stable. The wetting of the cornea starts to deteriorate again after this interval (drainage of the tear film, deposition of dust particles, etc.) and the described cycle starts from the beginning.

Figure 2:
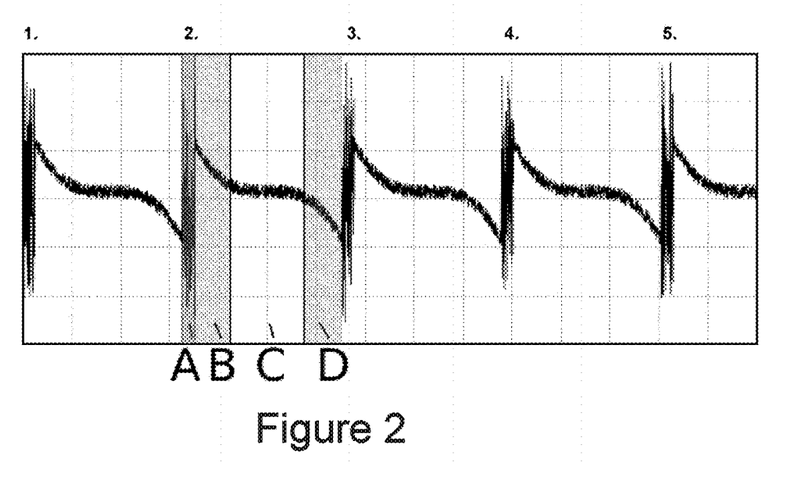
FIG. 2 depicts the individual phases of tear film dynamics on the eye, over five eyelid movement cycles.

In this respect, FIG. 2 depicts the individual phases of the tear film dynamics on the eye over approximately five eyelid movement cycles, as a temporal profile of the measurement of the radius of the cornea or of the precorneal tear film by use of a keratometer.

In this case, time is plotted on the abscissa and the radius of curvature of the cornea or of the precorneal tear film determined using the keratometer is plotted on the ordinate. According to the invention, this unveils the relevant dynamics of the tear film for the biometric measurement very well and can be subdivided into 4 phases, which repeat. In this case, phase A represents the eyelid movement, phase B represents the tear film stabilization, phase C represents the range of stable vision and phase D represents the tear film breakup.

Alternatively or else in addition, instead of the radius of curvature of the cornea or of the precorneal tear film, the axis position of the radii can also be represented on the ordinate with a similar variation within an eyelid movement cycle.

According to the invention, provision is firstly made to use only the measurement data from the range of stable vision (phase C) for the calculation of the radius of curvature from the keratometric measurement, and to discard the measurement data from phases A, B and D.

The phase of stable vision is present, in particular, should the change in the radii of curvature of the cornea or of the precorneal tear film be within the tolerance of R<+/−1%. If no measurement results can be collected in the individual case of a pathological cornea under the application of this restriction, the tolerance may also be increased to approximately <+/−5%. Conversely, the tolerance may also be restricted to approximately <+/−0.5% if sufficient measurement results are present, in order to be able to collect more accurate measurement data.

Figure 3:
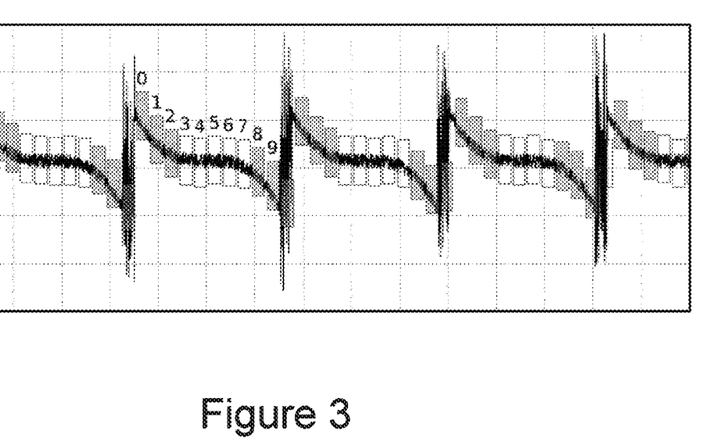
FIG. 3 depicts the continuous collection of measurement values with a typical individual measurement time of 0.1 s and a repetition rate of 10 Hz within continuous measurement windows (each with a duration of approximately 0.5-1.5 s and approximately 5-15 individual measurements) as gray and white marked boxes numbered 0 to 9.

FIG. 3 depicts in turn the continuous collection of measurement values (black measurement curve) according to the invention, with a typical individual measurement time of approximately 0.1 s and a repetition rate of approximately 10 Hz. Typically, the formation of a mean value and/or median value from approximately 10-15 individual measurements is envisaged. 10-15 individual measurement values (with 0.5-1.5 s measurement duration) are acquired per measurement window (illustrated as a box) and these are subsequently averaged (obvious outliers in these measurement values having already been removed previously). Currently, in the prior art, the mean value and/or median value from a measurement window supplies the output measurement result for the IOLMaster without the dynamic conditions in the eye being taken into account, and so said measurement result may have unwanted errors. According to the invention, measurement data with this individual measurement duration of 0.5-1.5 s are now acquired continuously and separately over an overall measurement duration of approximately 20 s over a plurality of eyelid movement cycles.

The representation shows the continuous measurement windows (each with a duration of approximately 0.5-1.5 s and approximately 5-15 individual measurements) as gray and white marked boxes numbered 0-9. Only measurement windows represented as adjacent boxes (numbers 3-7) marked in white, which exhibit the same mean values and/or median values (of the radius/axis of the front side of the cornea) within a tolerance of approximately 1%, can be assigned to measurement phase C as the range of stable vision of the patient within an eyelid movement cycle and are used according to the invention for further measurement data processing. The measurement results from measurement windows 0-2 and 8-9, which are represented by boxes marked in gray and which can be assigned to measurement phases B and D, are discarded.

The measurement phase C (or the measurement windows marked in white) are defined in that the change in the mean values and/or median values from one measurement window (of an individual measurement of 0.5-1.5 s) to the next measurement window is below a threshold of, e.g., approximately 1%.

Figure 4:
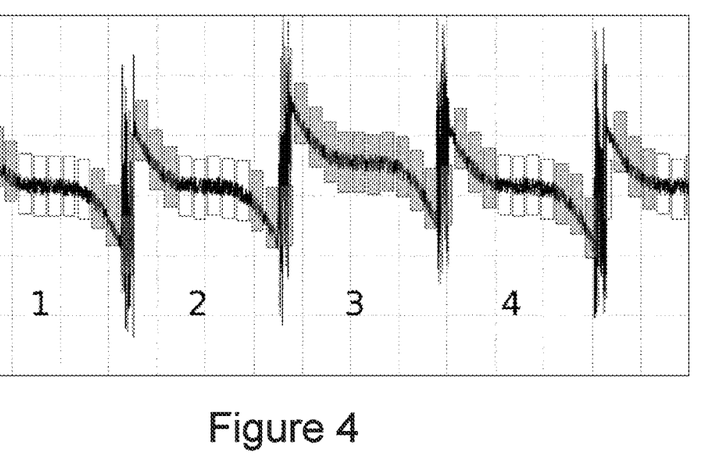
FIG. 4 depicts a comparison of the stable measurement values collected from a plurality of measurement phases over a plurality of eyelid movement cycles.

FIG. 4 shows a comparison of the measurement values collected over a plurality of eyelid movement cycles from a plurality of measurement phases, as a development of the invention. The mean values and/or median values or other aggregated values collected from a plurality of inherently stable measurement phases C over a plurality of eyelid movement cycles are compared and outliers that represent stable incorrect measurements are eliminated in order to output a more secured representative measurement value. At least 3 stable measurement phases C are provided for this evaluation.

This is a further stage of measurement data selection according to the invention, which carries out a comparative assessment of a plurality of eyelid movement cycles (4+ in diagram 4) and, for example, discards the inherently stable measurement phase over measurement windows 3-6 (boxes are marked in gray) in eyelid movement cycle 3.

Eyelid movement cycles 1, 2 and 4 as well as 5 in part supply overarching measurement windows (boxes marked in white) which exhibit the same mean values and/or median values (of the radius/axis of the front side of the cornea) within a tolerance of approximately 1%. These mean values and/or median values can be assigned with increased reliability to measurement phase C as the range of stable vision of the patient within a plurality of eye-movement cycles and are used for the further measurement data processing.

The above-procedure just described applies to one radius of curvature, that is to say to corneal surfaces without an astigmatism. Since many corneas have an astigmatism and hence a toric or ellipsoid surface shape, provision is made according to the invention for both radii of curvature $R_1$ and $R_2$ with their associated axes to be determined according to the procedure described. In this context, the two radii of curvature and their associated axes are determined simultaneously from the range of the respective stable vision.

Figure 5:
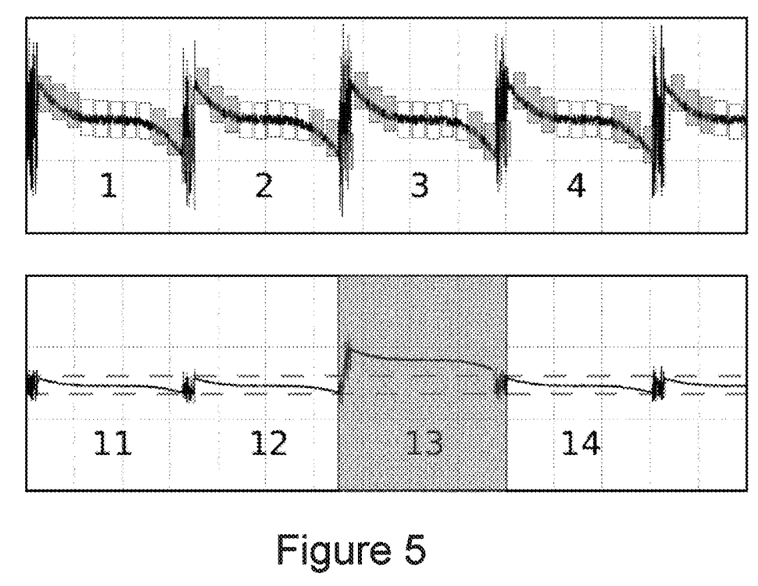
FIG. 5 depicts a representation of two parallel measurement quantities with temporal synchronization over a plurality of eyelid movement cycles.

FIG. 5 is a representation of two parallel measurement quantities with temporal synchronization over a plurality of eyelid movement cycles:
   top: radii of curvature/axes of the precorneal tear film of the front side of the cornea according to FIGS. 2-4 over 4 eyelid movement cycles (1-4)
   bottom: axis length (AL) of an eye determined over 4 eyelid movement cycles (11-14) by application of OCT or PCI by A and B scans, for example by use of the IOLMaster 700.

While a correct measurement of the radius of curvature of the front side of the cornea was obtained above within all stable phases C of the 4 eyelid movement cycles, the measurement of the eye length AL carried out synchronously therewith shows a tolerance range-exceeding measurement result for AL located outside of the specified measurement tolerance (2 dashed lines) in eyelid movement cycle 13, which measurement result can now be traced back not only to the tear film dynamics but also, for example, to an incorrect fixation of the patient during this cycle. According to the invention, this AL measurement value in eyelid movement cycle 13 is discarded while the values relating to the radius of curvature within the stable phase C in the same eyelid movement cycle 3 can initially be used for the measurement.

Figure 6:
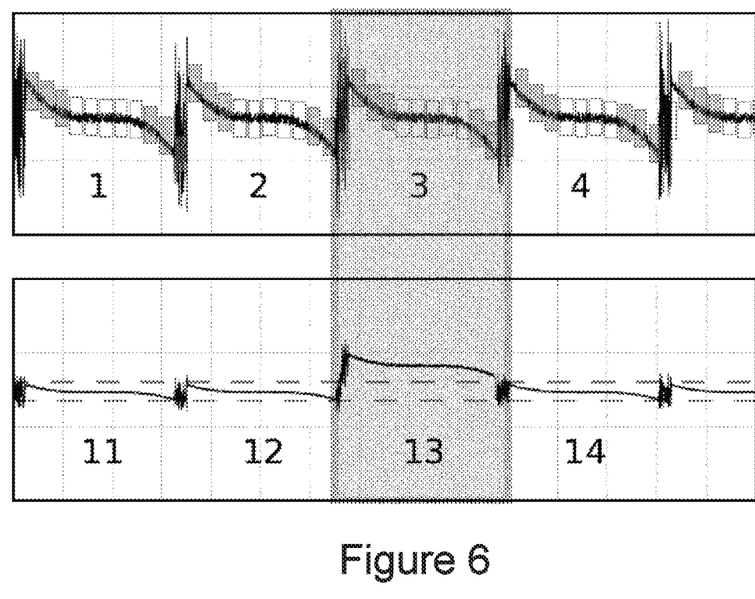
FIG. 6 depicts a representation according to FIG. 5, but with overarching selection of measurement values.

FIG. 6 is a representation of two parallel measurement quantities with temporal synchronization over a plurality of eyelid movement cycles according to FIG. 5, but with an overarching selection of data for an increased measurement accuracy and reliability of the measurement data:
   On account of the error-afflicted data situation regarding AL in eyelid movement cycle 13, the values relating to the radius of curvature within stable phase C in the same eyelid movement cycle 3 are also discarded.
   As is evident from the measurement data regarding AL in the lower figure, the AL is measured to be too long just after the eyelid movement and measured to be too short just before the eyelid movement, in relation to that measured in the known central range of known phase C. Accordingly, AL values only from phase C of the radius of curvature, measured in synchronized fashion, of the upper figure can be used for the evaluation, the other AL measurement values are discarded for the further evaluation. Apart from cycle 3/13, this applies to all other depicted cycles in FIG. 6.

According to a second example embodiment, the opening of the eyelid is monitored for the dynamic behavior of the eye in order to ensure that the eyelid is open far enough and there is no possible shadowing by eyelashes.

The procedure described above has assumed that all points of a keratometer or all rings of a topography system can be captured completely in the reflection image. However, what occurs often in practice is that, as a result of a too small opening, in particular of the upper eyelid, or else as a result of shadowing as a consequence of eyelashes, or as a result of local tear film breakup, individual reflection points or parts of Placido rings become unavailable for the evaluation. This effect may likewise lead to incorrect results regarding the radii of curvature and their axes. Moreover, a different number of keratometer points or a different image area of Placido rings may be registered during a plurality of measurements.

What should be provided in this respect according to the invention is that these deviations from the ideal full image in the keratometry and/or topography of the cornea, or else other measurement modalities, for example OCT pachymetry, are corrected statically and dynamically within a measurement series in the evaluation of the measurement results.

In particular, an algorithm is used to this end, which in the case of local image outages of:

for example <10% of the overall area of the corneal topography, carries out a fit for these areas on the basis of adjacent topography data, or in the case of >10% of the overall area of the corneal topography, discards these local data and no data are displayed there, in order to take these defects into account in the ideal data space of the biometry, and in order to avoid the effect thereof on an incorrect data output.

According to a third example embodiment, the fixation of the eye is considered for the dynamic behavior of said eye by virtue of measurements of the eye lengths being implemented continuously to this end and only measurement data which do not exceed a specified tolerance within a specified measurement time being output.

As already mentioned, patients are asked to fixate on a static target (usually a light dot) so that the eye length can be measured. This fixation depends on the understanding of the examination process, on the cataract grade of the crystalline lens and hence the visual acuity of the eye, and also on the ability of the patient to concentrate, which are often insufficient.

Furthermore, involuntary eye movements, the so-called saccades, are a cause for brief changes in the line of sight. Typically, the human visual behavior in static surroundings is characterized by an interaction of fixations and saccades. In the process, the instances where the eye is at relative rest relative to an observation object are referred to as fixations. The jumps of the eye for aligning the fovea centralis are referred to as saccades.

Saccades are ballistic movements which reach a speed of up to 900°/s, these movements having a duration of 2 ms to approximately 80 ms with amplitudes ranging from 2-50°. Thus, both patient-dependent insufficient fixation and involuntary saccades may prevent or only randomly facilitate a measurement along the visual axis of the eye.

The exact fixation of the eye on a target in the measuring device plays an important role, in particular when measuring the eye length and/or measuring the wavefront/refraction of the eye.

According to the invention, dynamic measurements of the eye lengths frequently longer than approximately 1 s (analogous to the defined measurement windows during keratometry with approximately 0.5-1.5 s there) are recorded, stable ranges of the eye lengths are selected in order only to average the measurement values of the eye length and/or to determine median values and bring those recorded within these stable regions to display.

Mean values and median values are specified in exemplary fashion in the description, but in principle other aggregated values can also be used. In this context, the clinical relevance will in each case determine what aggregated value is used.

In particular, provision is made for the eye length measurement or other OCT-based measurements with the precorneal tear film as a measurement point to be measured continuously over a period of time of at least 5 s to approximately 60 s, in particular approximately 20 s.

From the multiplicity of measurements with a repetition rate of at least 1 Hz to 10 kHz for OCT B scans and 1 kHz to 100 kHz for OCT A scans, only those measurement values are brought to the evaluation which within a continuous measurement time of at least 1 s to approximately 20 s do not exceed a tolerance of the measured eye length of +/−50 μm, or in another example +/−10 μm.

Hence, the capture of physiologically stable measurement phases in the case of a correct fixation of the eye is ensured and a physiologically correct measurement value of the eye length can be collected.

In addition to this 3rd example embodiment, provision is made for an exact fixation to be identified on the basis of an OCT retinal scan (see FIG. 7) by virtue of the presence of the foveal pit being recognized automatically by application of an image processing algorithm. The axis length is determined from the measurement data only if a foveal pit is recognized. If no foveal pit is recognized, all data collected dynamically within this measurement time period are discarded. In respect of the lateral width of the retinal scan, provision is made for a small region of approximately 1.5 mm to be used, and for only the presence of the foveal pit to be checked therewithin. Furthermore, in particular in the case of a retinal scan >1.5 mm, provision is made for the relative position of the foveal pit to be assessed for the lateral scan and for only those measurement results of the AL to be used which were collected in the case of a central position of the foveal pit with a tolerance of +/−0.5 mm. In the case of asymmetric scans of the biometer, the tolerance range should be related to the expected position of the fovea.

Figure 7:
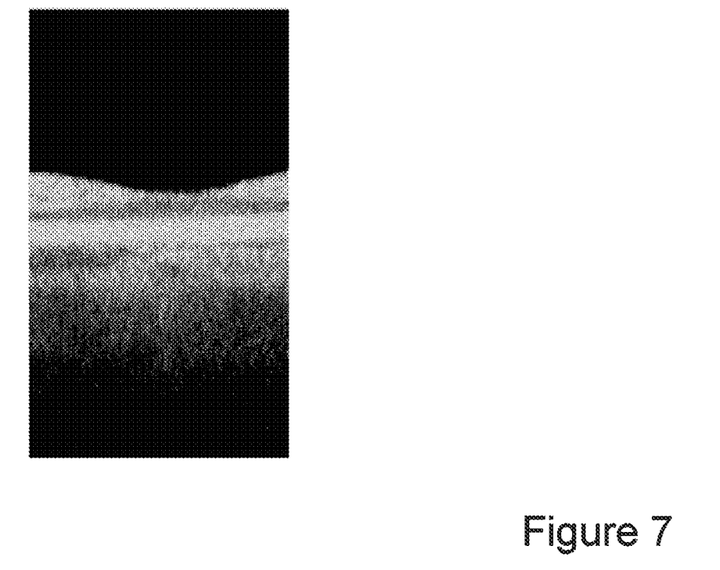
FIG. 7 depicts an OCT scan of the retina with foveal pit as fixation check during the measurement of the eye length.

FIG. 7 shows an OCT retinal scan with a foveal pit as a fixation check during the measurement of the eye length AL. In this case, it is desirable to also carry out the scan of the fovea at the same time as the AL measurement. Should this not be possible with the available OCT technology, a temporal succession of AL measurements and associated scans of the fovea should be provided closely together in time.

By way of example, a scan of the fovea is envisaged within at least one eye lid movement following the AL measurement. If both the AL measurement and a fovea scan are carried out within an eyelid movement cycle with tear film phases A-D, there is increased reliability of the fixation check in relation to the case where the scan of the fovea is only carried out in a subsequent eyelid movement cycle. If the scan of the fovea provides a faulty fixation result, the AL measurements before and after this scan of the fovea should be discarded; if it is correct, the AL measurement results preceding and following this can initially be used further on the basis of this selection criterion.

According to a fourth example embodiment, the dynamic behavior of the eye is taken into account on the basis of its accommodation by virtue of continuous measurements of the anterior chamber depth being implemented in this respect. According to the invention, only those measurement data for which the anterior chamber depth has a value that is as large and as stable as possible within a specified measurement time are output.

The accommodation of the eye also causes dynamics, in particular of the lens shape and the lens position, but partially also in terms of the corneal shape of the eye. The patients are requested to look into the distance, for example with the aid of a fixation image, in order to be able to capture the desired disaccommodated state of the eye. However, so-called "device myopia" also referred to as instrument myopia, is known, which in the patients examined on the devices triggers a certain near accommodation despite these efforts, and which leads to measured values being shifted in the direction of myopia. In particular, this can be used to explain the deviations of the order of −0.5 dpt between subjectively gathered refraction and objectively measured refraction using an autorefractor.

To be able to exclude device myopia or the dynamics of accommodation in the case of an eye fixated at infinity (or set up on the biometer), provision is made according to the invention for in particular the dynamics of the relative position of the front side of the eye lens in relation to the cornea, or the precorneal tear film to be determined.

The plausible assumption can be made in the case of accommodation that the lens moves in the direction of the cornea and the front side of the lens is curved more pronouncedly. Both effects lead to a shortening of the distance between the front side of the cornea and the front side of the crystalline lens, that is to say the anterior chamber depth. Consequently, according to the invention, the dynamically determined values of the anterior chamber depth are examined for stable ranges with the longest possible anterior chamber depth in order to select stable and physiologically representative measurement data of the anterior chamber depth and also the data of the lens radii and the lens thickness, which are connected therewith in this case.

Figure 8:
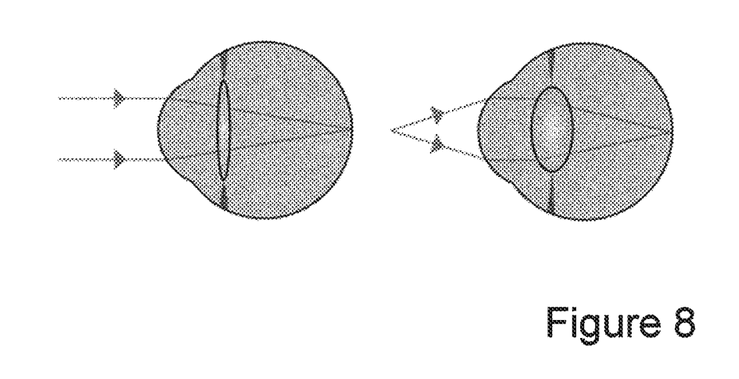
FIG. 8 depicts a schematic comparison of the conditions in the eye in the case of disaccommodation (left) and accommodation (right).

In this case, FIG. 8 shows a schematic comparison of the conditions in the eye in the case of disaccommodation (left) and accommodation (right).

Instead of the anterior chamber depth, continuous measurements of lens thickness and/or lens radii and/or lens curvatures within a measurement time of for example 1 s-20 s are also possible, as these are likewise modified by accommodation.

The disaccommodated state of the eye is characterized by:
the greatest anterior chamber depth,
the smallest lens thickness,
the largest lens radii and
the smallest curvature of the lens surfaces.

According to a fifth example embodiment, the dynamic behavior of the eye is taken into account on the basis of its adaptation by virtue of measurements of the pupil diameter being implemented continuously to this end and only measurement data in which the pupil diameter has a stable value within a specified measurement time being output.

In the case of the eye, adaptation is understood to mean its adaptation to the luminance prevalent in the visual field. In the case of brightness differences, the incident amount of light is adjusted by constricting or dilating the pupils using the iris muscles. When the eye is measured, the pupil diameter therefore depends on the brightness in the room and on the brightness of the fixation targets in the measuring device.

In particular, the adaptation of the eye can be used on the basis of the first Purkinje image on the cornea to assign its position within the respective pupil and hence the point of intersection of the visual axis with the cornea to the measurement data.

In known biometric measuring devices, a pupillometry is usually available during the measurement of other eye parameters. However, these data of the pupil diameter are only assigned to the other measured eye parameters without further processing.

According to the invention, a variation of the pupil diameters by way of different luminous intensities at the ocular to the biometric measuring apparatus is provided. Thus, for example, the pupil diameter can be varied from approximately 2 mm to approximately 7 mm and the physiologically correct measurements dynamically selected according to all previously discussed parameters can be implemented in each case.

From the measurement results, the other biometric values can then be assigned to each pupil diameter and the biometry can be dynamic on account of the adaptation of the eye.

In this pupillometry, provision is further made, on the basis of the first Purkinje image on the cornea, for its position within the respective pupil and hence the point of intersection of the visual axis with the cornea to be assigned to the measurement results. In the process, this point of intersection of the visual axis of the cornea is registered not only within the respective pupil diameters but additionally also with respect to the stable limbus diameter or the latter's center. A variation in the first Purkinje image within the pupil diameter is a sign of an unstable fixation of the patient during the measurement and, according to the invention, may likewise be used as a selection criterion for the selection of physiological stable measurement values during a stable fixation.

Moreover, provision is made for physiologically correct measurement data to be filtered out of the dynamically recorded measurement data by way of a plurality of criteria and for only the measurement data that meet all selection criteria to be transmitted to the output of the measuring device.

According to the invention, these selection criteria may be designed to be adjustable. By way of example, a measurement precision of the individual parameters of 0.1%, . . . 1% or 5% may be preselected. Thus, a very high measurement precision requires the use of many selection criteria while a lower measurement precision is also facilitated with individual selection criteria within a short measurement time Therefore, according to example embodiments of the invention, provision is further made for the measurement of the keratometry to be implemented as described above and for, in a time-coupled process, the eye lengths to be dynamically determined on the basis of optical coherence tomography (OCT) by application of A scans or else B scans.

In this case, typical rates of 1 kHz-100 kHz for A scans and of 1 Hz-10 kHz for B scans are provided. Furthermore, a holoscopic OCT measuring technique can also be used. Since the relative position of the interface between the stable precorneal tear film and air is an important measurement point for the eye length and also for all other distances and lengths along the visual axis and/or optical axis of the eye, the measurement values of the eye lengths which were recorded within the time interval of stable vision determined by dynamic keratometry are now brought to the evaluation.

This recording can be implemented multiple times within a plurality of stable regions and the multiplicity of measurement values can subsequently additionally be averaged, for example, and/or median values can be determined, in order to obtain a best value in respect of the physiological correctness and robustness.

The example method according to the invention provides a solution with which physiologically correct, representative and robust biometric measurement data of an eye can be acquired on the basis of various measuring methods. In this case, the measurement data acquisition considers the optical-physiological state of the eye and realizes automated data acquisition and data evaluation.

The determination of the optical-physiological state of the eye is based on the consideration of the dynamic behavior of the eye. To this end, the dynamic behavior of the eye is recorded continuously over the measurement time at the highest possible repetition rate, The limits for the phase of stable vision are defined from the analysis of the individual phases of the dynamic behavior and ultimately only the measurement data of the individual measurement quantities which were acquired during the phase of stable vision are output.

The following should be mentioned in this context as the most important selection criteria for acquiring a physiologically correct state of the eye:

A correct tear film on the basis of topographically determined measurement data.

A correct eye length with an exact fixation of the eye on the basis of tomographically determined measurement data.

Correct values of the anterior chamber depth, lens thickness, lens radii or lens curvatures on the basis of tomographically determined measurement data.

The invention claimed is:

1. A method for determining physiologically correct biometric measurement data of an eye taking account of dynamic behavior of said eye, comprising:
    continuously recording measurement data of individual measurement quantities over a measurement time spanning several blink cycles and extending over a time approximating 20 seconds at a selected repetition rate approximating 10 Hz for dynamic keratometry, a selected repetition rate of 1 Hz to 10 KHz for OCT based B-scans, a selected repetition rate of 1 KHz to 100 KHz for OCT based A-scans or a combination of the foregoing,
    automatically analyzing individual phases of the dynamic behavior of the eye and defining limits for a phase of stable vision based on the individual measurement quantities by tolerance specifications for the measurement data for the individual measurement quantities; and
    outputting only the measurement data of the individual measurement quantities acquired during the phase of stable vision.

2. The method as claimed in claim 1, further comprising recording at least one of the following measurement data:
    topographic measurement data,
    tomographic measurement data,
    pachymetric measurement data,
    refractive measurement data and
    biometric measurement data.

3. The method as claimed in claim 2, further comprising displaying only the biometric, topographic, tomographic, pachymetric or refractive measurement data which were recorded in the phase of stable vision, and forming a mean value and/or median value or any other aggregated value from individual measurements.

4. The method as claimed in claim 3, further comprising recording biometric topographic, tomographic, pachymetric and refractive measurement data in a time-coupled process.

5. The method as claimed in claim 1, further comprising analyzing the dynamic behavior of the eye on a basis of at least one of the following criteria:
    tear film,
    opening of the eyelid,
    fixation,
    accommodation and
    adaptation.

6. The method as claimed in claim 5, further comprising recording the tear film for the dynamic behavior of the eye, by virtue of measuring and analyzing the radius of curvature and/or the associated axes of the precorneal tear film or of the cornea in each case between two eyelid movements.

7. The method as claimed in claim 5, further comprising recording the opening of the eyelid for the dynamic behavior of the eye, in order to ensure that the eyelid is open far enough and if there are local image outages of:
    <10% of the overall area of the corneal topography, carrying out a fit for these areas on the basis of adjacent topography data, or
    >10% of the overall area of the corneal topography, discarding these local data and displaying no data there.

8. The method as claimed in claim 5, further comprising considering the dynamic behavior of the eye on the basis of fixation, implementing measurements of the eye lengths continuously to this end and outputting only measurement data which do not exceed a specified tolerance within a specified measurement time.

9. The method as claimed in claim 5, further comprising considering the dynamic behavior of the eye on the basis of its fixation, implementing measurements of the eye lengths continuously to this end and outputting only measurement data in which the fovea could be detected within certain tolerances.

10. The method as claimed in claim 5, further comprising implementing the measurements of the eye length continuously, on an OCT basis, the measurement data to be output not exceeding a tolerance selected from a group consisting of +/−50 µm, and +/−10 µm, within the measurement times.

11. The method as claimed in claim 5, further comprising analyzing the dynamic behavior of the eye with accommodation taken into account, implementing measurements of the anterior chamber depth continuously to this end and outputting only measurement data in which the anterior chamber depth has a value that is as large and as stable as possible within a specified measurement time.

12. The method as claimed in claim 5, further comprising analyzing the dynamic behavior of the eye with accommodation taken into account, implementing measurements of lens thickness, lens radii or lens curvatures continuously to this end and outputting only measurement data in which the anterior chamber depth has a value that is as large and as stable as achieved within a specified measurement time.

13. The method as claimed in claim 5, further comprising analyzing the dynamic behavior of the eye with accommodation taken into account, implementing measurements of the lens thickness continuously to this end and outputting only measurement data in which the lens thickness has a value that is as small and as stable as achieved within a specified measurement time.

14. The method as claimed in claim 5, further comprising analyzing the dynamic behavior of the eye with its adaptation taken into account, in that measurements of the pupil diameter are implemented continuously to this end and only measurement data in which the pupil diameter has a stable value within a specified measurement time are output.

15. The method as claimed in claim 5, further comprising using the first Purkinje image on the cornea to detect a position thereof within the respective pupil and/or iris, and hence assigning a point of intersection of the visual axis with the cornea to the measurement data.

16. The method as claimed in claim 15, further comprising using variation in the relative position of the first Purkinje image in relation to the pupil center and/or iris center to determine stable phases of fixation.

17. The method as claimed in claim 1, further comprising selecting the measurement time for continuously recording the measurement data of the individual measurement quantities from a group consisting of at least 0.5 s, at least 20 s and selecting overall measurement time for recording all measurement data to be a few minutes long.

18. The method as claimed in claim 1, further comprising determining the limits for the phase of stable vision from analysis of the individual phases of the dynamic behavior of the eye on a basis of a criterion.

19. The method as claimed in claim 1, further comprising implementing the analysis of the individual phases of the dynamic behavior of the eye on the basis of various criteria and determining limits for the phase of stable vision from the overlap thereof.

20. The method as claimed in claim 1, further comprising analyzing the individual phases of the dynamic behavior of the eye on the basis of various criteria and defining different limits for the phase of the stable vision and using only the measurement data of the individual measurement quantities recorded during the various phases of stable vision to form a mean value and/or a median value or to form any other aggregated value and are output.

21. The method as claimed in claim 20, wherein the phase of stable vision is present should the change in the radii of curvature of the cornea or of the precorneal tear film be within a tolerance of $R<+/-1\%$.

* * * * *

UNITED STATES PATENT AND TRADEMARK OFFICE
CERTIFICATE OF CORRECTION

| | |
|---|---|
| PATENT NO. | : 12,426,778 B2 |
| APPLICATION NO. | : 17/762537 |
| DATED | : September 30, 2025 |
| INVENTOR(S) | : Mäusezahl et al. |

Page 1 of 1

It is certified that error appears in the above-identified patent and that said Letters Patent is hereby corrected as shown below:

In the Specification

Column 1, Line 10, delete "2019" and insert --2019,--

Column 12, Line 33, delete "physiological" and insert --physiologically--

Column 12, Line 48, delete "time" and insert --time.--

Column 13, Line 15, delete "rate, The" and insert --rate. The--

In the Claims

Column 13, Lines 50-51, delete "quantities; and" and insert --quantities, and--

Column 13, Line 60, delete "data and" and insert --data, and--

Column 14, Line 10, delete "accommodation and" and insert --accommodation, and--

Signed and Sealed this
Thirtieth Day of December, 2025

John A. Squires
*Director of the United States Patent and Trademark Office*